United States Patent [19]

Prosen

[11] Patent Number: 4,511,263
[45] Date of Patent: Apr. 16, 1985

[54] BOMB-TYPE CONDUCTION CALORIMETER

[76] Inventor: Edward J. Prosen, 621 Warfield Dr., Rockville, Md. 20850

[21] Appl. No.: 513,074

[22] Filed: Jul. 12, 1983

[51] Int. Cl.³ .............................................. G01N 25/22
[52] U.S. Cl. ........................................ 374/38; 374/36; 374/33
[58] Field of Search .................. 374/31, 32, 33, 34, 374/36, 38, 41

[56] References Cited

U.S. PATENT DOCUMENTS

| | | | |
|---|---|---|---|
| 673,325 | 4/1901 | Parr | 374/38 |
| 931,189 | 8/1909 | Emerson | 374/38 |
| 1,136,360 | 4/1915 | Parr | 374/38 |
| 1,247,998 | 11/1917 | Parr | 374/34 |
| 3,059,471 | 10/1962 | Calvet . | |

Primary Examiner—Steven L. Stephan
Assistant Examiner—David R. Schuster
Attorney, Agent, or Firm—Parkhurst & Oliff

[57] ABSTRACT

A bomb-type conduction calorimeter consists of a bomb separated from a substantially infinite heat sink by several heat flow detecting elements. The bomb is enclosed by an inner copper box having a cylindrical interior and a polygonal exterior. The inner copper box is enclosed by an outer copper box having a polygonal interior. The heat flow detecting means may be several thermopiles in contact with the inner and outer polygonal surfaces. The infinite heat sink may be a constant temperature water bath. Heat flow directly from the test substance is measured, as opposed to the heat flow dissipated to the environment of the bomb. The calorific values determined are independent of the amount of water in the water bath.

10 Claims, 5 Drawing Figures

BOMB-TYPE CONDUCTION CALORIMETER

BACKGROUND OF THE INVENTION

This invention relates to an apparatus whereby the calorific value or heat of combustion of a test substance may be determined. More specifically, this invention relates to a device having a bomb in which the combustible substance to be tested is ignited. The heat generated by combustion is then determined by comparison to a known standard.

The measurements of heat of combustion or calorific value has for many years been carried out by means of either adiabatic or isoperibol bomb calorimeter systems. In both of these systems, a steel or illium bomb is utilized to containerize the ignition and combustion of a test sample at high pressure. The bomb is immersed in a water filled vessel, having accurate water temperature measuring means therein. The water is circulated within the vessel by means of a stirrer. The vessel and bomb are then placed within a water jacket, an air space forming a gap between the water vessel and the water jacket.

Both of the above prior art systems require elaborate means for controlling the water jacket temperature. With the isoperibol system, it is necessary to maintain the water jacket at a substantially constant temperature and corrections for heat leak must be made. The water jacket in the adiabatic type systems must follow the calorimeter temperature very closely. In these systems, the water jacket must be capable of rapidly adjusting to eliminate temperature differentials between the water jacket and the calorimeter.

In both of these systems the heat of combustion of the tested substance is determined by calculating the change of temperature of the water in the water vessel and multiplying that change by a predetermined calibration constant. The calibration constant is determined by burning a known standard, such as benzoic acid, and observing the temperature change. The ratio of the test substance temperature change to the standard temperature change is then assumed to be directly proportional to the ratio of the heats of combustion.

Because the change in temperature is directly related to the heat capacity of the water in the water vessel and the calorimeter itself, the amount of water in the water vessel must be accurately weighed and measured. Additionally, the accuracy of the heat of combustion, as calculated, could be no greater than the accuracy of the thermometer or temperature measuring device utilized in the determination.

Bomb-type calorimeters are generally utilized to test relatively large samples, measuring energy of the order of $4 \times 10^4$ Joules. Devices for measuring relatively large energy emissions are termed "macrocalorimeters". An entirely different methodology is implemented in the measurement of extremely small energy emissions, i.e. of the order of $10^{-6}$ to $10^{-2}$ Joules.

The devices employed for measuring these small energy emissions are appropriately termed "microcalorimeters". These devices directly measure the heat emitted from a sample, as opposed to the heat dissipated therefrom to another body. Heat energy is carried away from the test substance by sets of series connected thermocouples, termed thermopiles. The heat thus emitted is dissipated to a substantially infinite heat sink, usually an aluminum block. The thermopiles generate a voltage which is proportional to the temperature gradient across their junctions. Because all or most of the heat is carried through the thermopiles by conduction, the voltage of the thermopiles is directly proportional to the power emitted from the test substance. An integration of this power with respect to time results in the total energy emitted by the test substance.

In a known application of a device of this type, the open-circuit self-discharge heat losses of tiny batteries, as used in the pace-maker industry, may be determined. In these applications, powers as low as 0.1 $\mu$W have been measured.

The use of the above-mentioned methodology has heretofore not been expanded beyond the field of microcalorimetry.

SUMMARY OF THE INVENTION

Accordingly, it is an object of the present invention to provide a bomb type calorimeter for measuring relatively high energies, based on the heat energy directly emitted by a combustible test substance or other reactant, rather than on the heat energy dissipated to an adjacent environment. Further, it is an object of the present invention to eliminate the need to accurately measure or weigh water and to eliminate the need for extremely accurate thermometers in the heat of combustion determination. It is an additional object to provide a fast turnaround time between consecutive heat of combustion calculations.

These and other objects are satisfied by the present invention which includes a calorimeter bomb which emits energy by conduction through thermopiles to an infinite heat sink. More specifically, a steel or illium bomb having a removable lid is provided to containerize the combustion of a test sample supported within. The bomb, having a circular cylindrical exterior, is placed within an inner copper box. An oil or water conduction layer fills a gap between the exterior surface of the bomb and an inner copper box. An outer copper box containerizes the inner copper box, the gap between the boxes being filled by several solid state heat flow detecting elements or thermopiles. Optimally, all of the heat is transferred by conduction through the thermopiles and dissipated into the infinite heat sink. The infinite heat sink is comprised of a water bath maintained at a constant temperature by insulating its external surface, and providing a stirrer, a heating coil, and a cooling coil.

As a consequence of the heat energy passing through the thermopiles, a voltage is emitted and recorded as a function of time. The result obtained by integrating this voltage with respect to time is directly proportional to the heat of combustion or other energy emission of the test substance, the proportionality constant being determined through the testing of a known standard or by electrical energy calibration.

DETAILED DESCRIPTION OF THE INVENTION

The following is a detailed description of one preferred embodiment of the present invention, and should be understood to be an example only.

Figure 1:
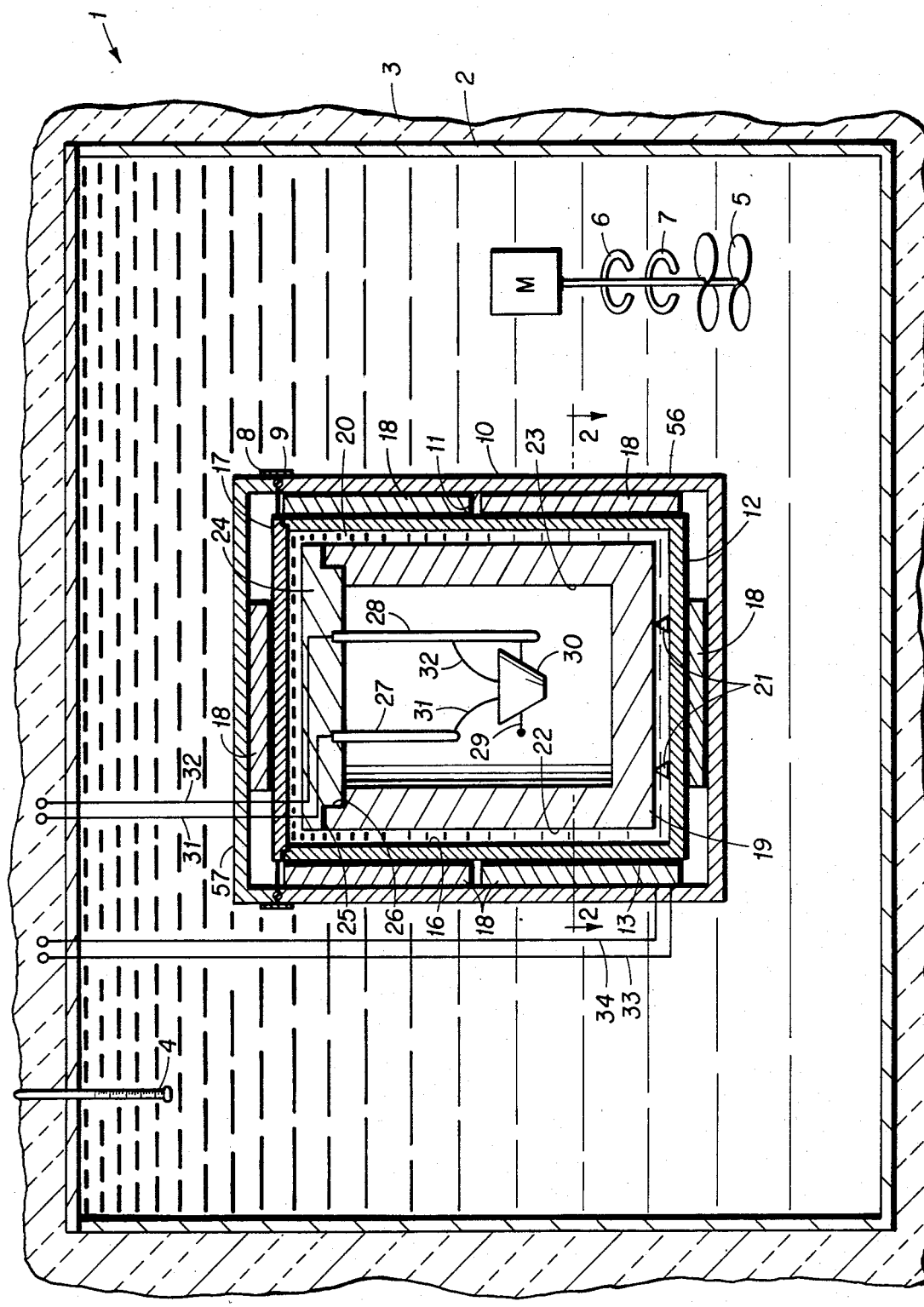
FIG. 1 is an elevational cross-section of the entire bomb-type conduction calorimeter apparatus of the present invention in schematic form.

The bomb-type conduction calorimeter of the present invention is depicted in FIG. 1 and is designated generally by reference numeral 1. In that device, a water bath 2, is surrounded with suitable insulation 3 and filled with a large volume of water. The water volume and control is selected so as to remain at a substantially constant temperature when heat is dissipated thereto. The water bath constitutes a substantially infinite heat sink for the present invention. A thermometer or other temperature sensing device 4 is provided to monitor the temperature of the water bath to insure that it remains constant within approximately ±0.0005 K. A motor driven stirrer 5, a heating coil 6, and a cooling coil 7 are utilized to correct for straying temperatures detected by the temperature sensing device. An outer copper box 56 is suspended by any appropriate means (not shown in the Figure) within the water bath, copper being used because of its good thermal diffusivity and thermal conductivity. Silver or aluminum could alternatively be employed. The outer copper box has a lid 57 secured by several locks 8, water leakage being prevented by O-ring 9 at the junction of the box and the lid. The outer copper box has a circular cylindrical exterior vertical wall 10 and a polygonal interior vertical wall 11 (See FIGS. 2 and 3). An inner copper box 12 is encased by the outer copper box 56 to form the "sensor box". The inner copper box has a polygonal outer vertical surface 13, with its faces 14 being parallel to the faces of the inner polygonal surface of the outer copper box. The inner copper box has a circular cylindrical vertical interior surface 16 and a notched lid 17 in good thermal contact with the remainder of the inner copper box. The median thickness of both the inner and outer copper boxes should preferably be approximately ⅛ inch.

Figure 2:
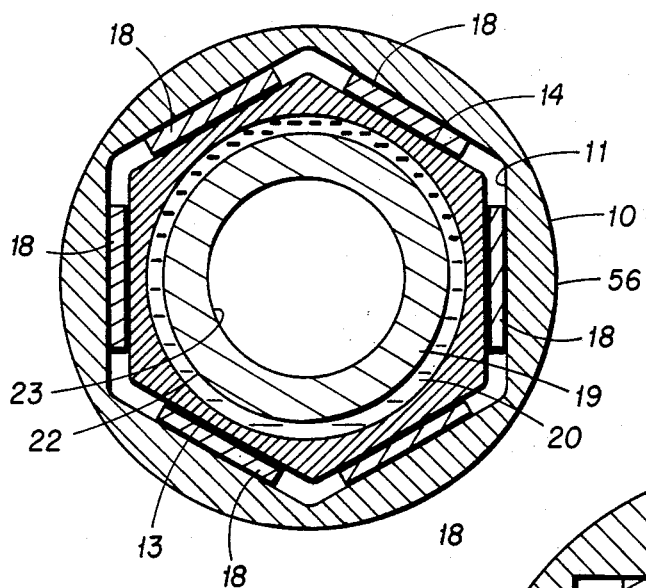
FIG. 2 is a cross-sectional view of the calorimeter excluding the water bath, taken along line II—II of FIG. 1.
Figure 3:
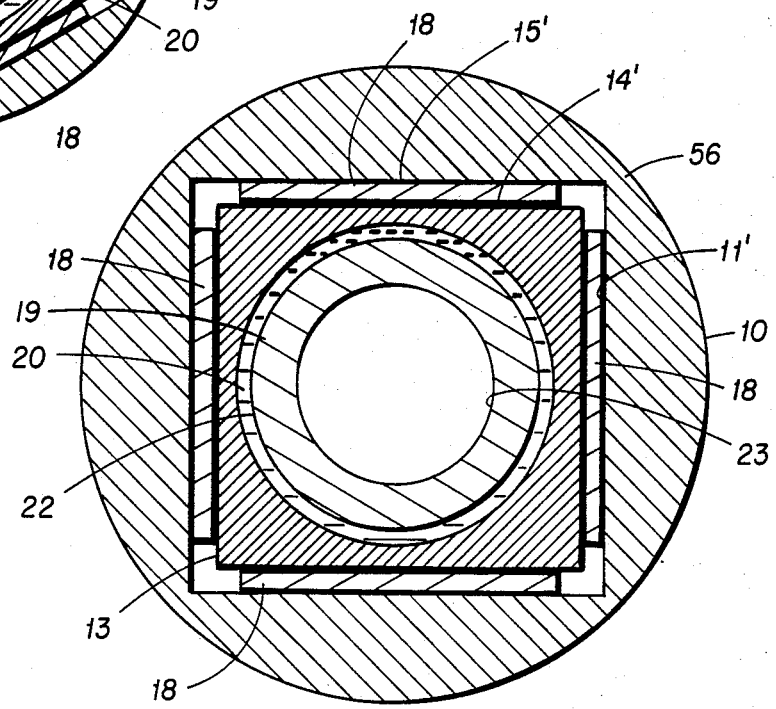
FIG. 3 is a similar cross-section to that of FIG. 2 showing an alternative embodiment of the present invention.

The upper, lower, and peripheral space between the inner and outer boxes is filled with heat flow detecting devices, leaving as little dead space as is practical. The heat flow detecting devices may be of any known type of metal or solid state device, such as N-type and P-type Bismuth-Telluride thermopiles. The thermopiles are comprised of several series connected thermocouples, in a manner well known in the art. By limiting the amount of dead space, convection is minimized, thus allowing most of the heat transfer to be in the form of conduction through the thermopiles. The heat transfer by radiation is minimal. As seen in FIGS. 1-3, the thermopiles are adjoined on their exterior face to the inner surface 11 of the outer copper box and to the inner surface of the lid 7. They are similarly joined to the outer surfaces 13 of the inner copper box 12. The thermopiles located in the vertical space between the inner and outer boxes, are sandwiched by and fixed to polygonal faces 14, 11 on their respective interior and exterior faces. The outer 57 and inner 17 copper box lids are joined by at least one thermopile 18 and removable as a unit.

A bomb 19, made of steel or illium, is insertable to the inner copper box with a small space 20 therebetween. The bomb has a circular cylindrical exterior, the bottom end of which rests on supports 21 to maintain the gap between the lower face of the bomb and the lower face of the inner copper box. The gap 20 forms a conduction layer and is filled with oil or water to conduct energy from the bomb through the layer to the inner copper box.

Bomb 19 has a cylindrical outer surface 22, a cylindrical inner surface 23, and a removable lid 24. The bomb lid 24 has a notch 25 formed therein to mate with notch 26 on the cylindrical portion of the bomb, positively locating the lid in good thermal contact. Metallic rods 27, 28 are fixedly located to the lid to extend inside the cavity of the bomb. A sample cup 30 is mounted to rod 28 by sample cup mount 29. Ignition wire leads 31, 32 run from the sample cup through the metallic rods and to the bomb lid. The ignition wires continue to run from the lid through the inner and outer copper box lids in any suitable known manner. Thermopile wire leads 33, 34 exit the outer copper box in a manner similar to ignition wires 31, 32.

As described above, FIG. 2 is a cross sectional view of the bomb, the conduction layer, the inner copper box, the thermopiles, and the outer copper box taken along line II—II of FIG. 1. FIG. 3 pertains to an alternative embodiment to the present invention also taken along line II—II of FIG. 1. Like features in FIG. 3 are given the same reference numerals as above. A prime notation has been adopted for those features slightly modified. In particular, FIG. 3 pertains to an embodiment wherein square, and not hexagonal, surfaces surround the thermopiles 18.

It should also be recognized, that because the water bath is no more than an infinite heat sink and does not enter into the heat of combustion calculations, several calorimeter devices might be utilized in a single water bath. Additionally, for applications wherein extremely high temperatures are anticipated, oil could be used in lieu of the water in the water bath, oil having a significantly higher boiling temperature. For even higher temperatures, aerated sand or an electrical tube furnace could be implemented.

In testing certain substances, e.g., sulfur and halogen compounds, it is necessary that the calorimeter have the capacity to rotate and tumble, mixing its contents. Heretofore such movement has created difficulties in that the correction for the mixing energy imparted to the water vessel could not be easily determined. Because the water bath in the present invention is no more than an infinite heat sink, mixing energy imparted to the water is of no consequence.

Figure 5:
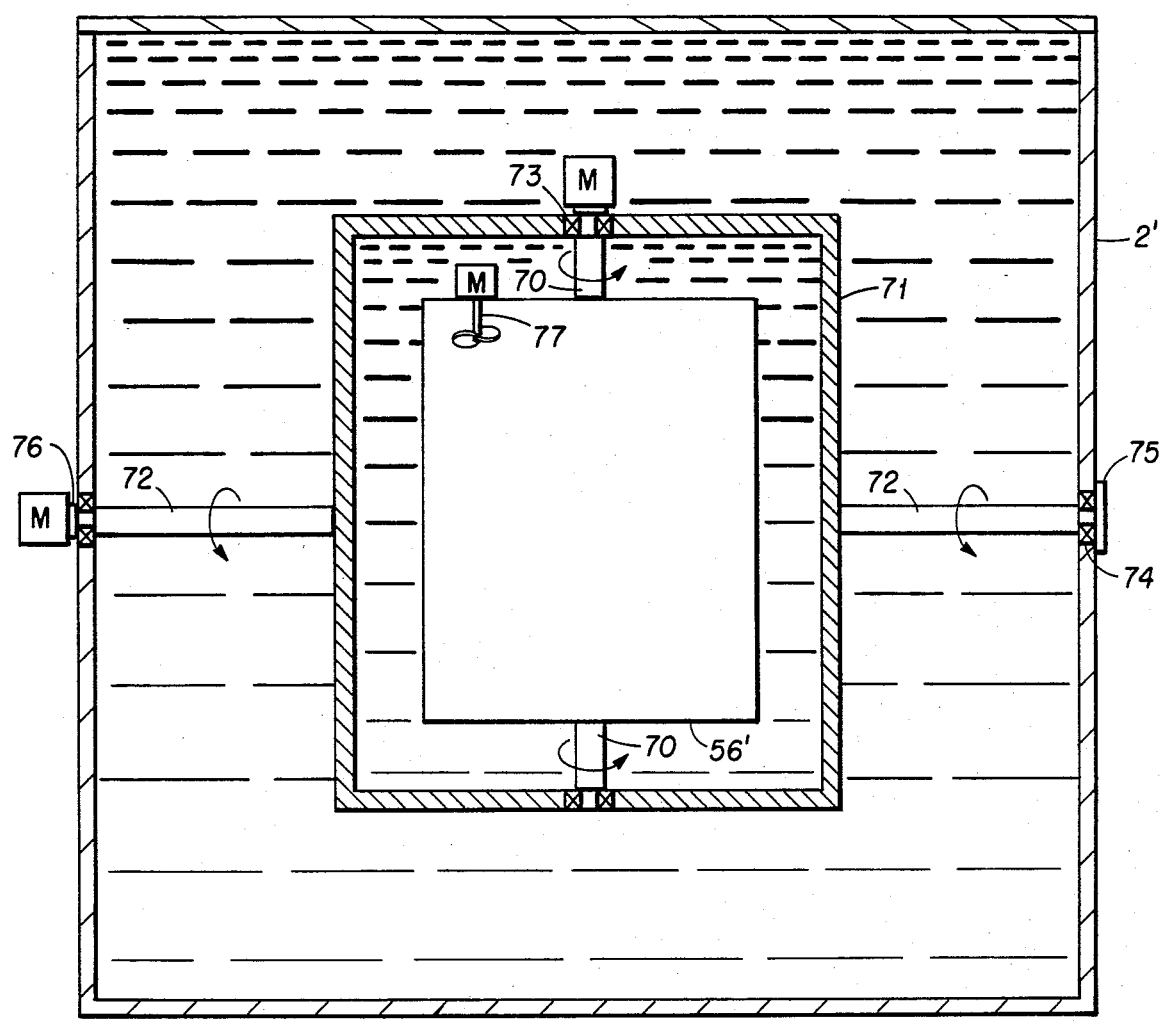
FIG. 5 is an elevational cross-section of an alternative embodiment of the bomb-type conduction calorimeter apparatus of the present invention.

FIG. 5 corresponds to an alternative embodiment of the present invention wherein the calorimeter 56' may be rotated about a vertical shaft 70 affixed thereto within a cage 71. Similarly, cage 71 is journalled about cage shafts 72 within the water bath 2'. Suitable bearings 73, 74 and seals 75, 76 are provided in a manner well known in the art. Motors, or any other appropriate driving means cause the calorimeter and cage to rotate and tumble, respectively.

The apparatus of the present invention is not limited in scope to the determination of heats of combustion. Any reaction wherein energy is emitted from a containerized vessel may be tested with the calorimeter discussed herein. Reactions involving mixing of solutions may be tested with only minor modifications to the present apparatus. A stirrer 77 may be placed within the calorimeter if an appropriate shaft entry is provided. Additionally, specialized reaction vessels may be formed to fit inside the sensor box. In this manner, heats of absorption and adsorption may be tested.

The bomb-type conduction calorimeter of FIGS. 1-4 also has application in measuring very slow reactions. For example, the heat of hydration of setting cement may be followed for weeks at a time, so long as the water bath is maintained at a constant temperature.

Figure 4:
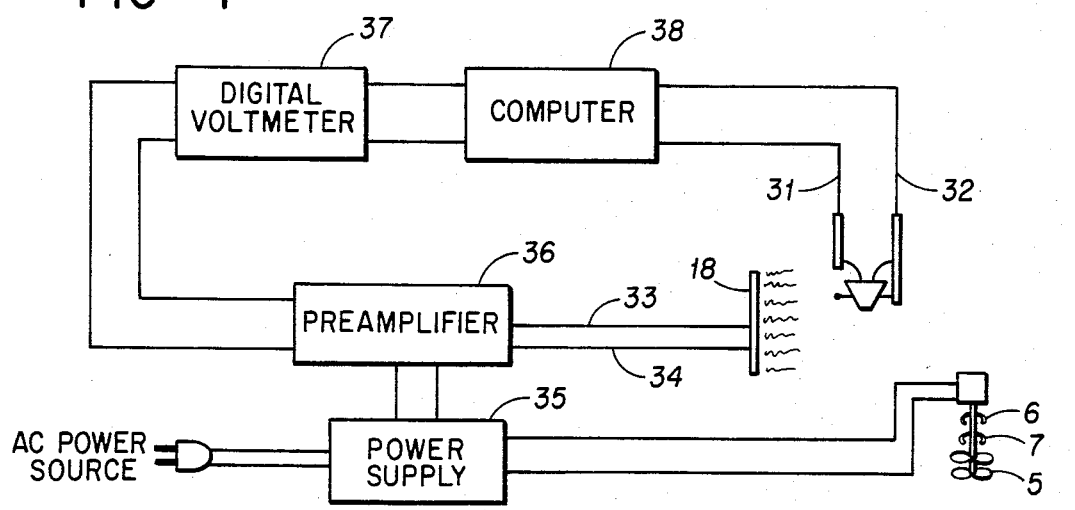
FIG. 4 illustrates, in schematic form, the circuitry of the present invention.

FIG. 4 is a schematic representation of the circuitry and wiring of the present invention. Ignition wires 31, 32 are fired by and fed to a computer 38 which also receives data from a digital voltmeter 37. The data received by the digital voltmeter is a voltage as a function of time, generated by thermopile 18 and transmitted through wires 33, 34, and through preamplifier 36. As previously described, the thermopiles 18 may be N-type and P-type solid state thermopiles with an output of 400 $\mu V/K$. This voltage output is increased by a gain of 1,000 in the preamplifier to minimize the noise level and maximize the stability of the output. The preamplifier should be in good contact with the water bath to maintain it at a constant temperature. For tests yeiding large energy emissions and correspondingly high voltages, the preamplifier may be dispensed with. The data from the digital voltmeter is fed to the computer where it is recorded as a function of time. The computer functions to trigger the ignition wires when an equilibrium temperature in the calorimeter and water bath has been attained. The water bath is maintained at a constant temperature by heating coil 6 and cooling coil 7. Homogeneity of the temperature is maintained by use of stirrer 5.

The thermopiles should be designed so as to minimize the time constant of the calorimeter and to maximize its sensitivity. An apparatus having a small time constant will conduct the total heat from the combustion of the test substance in a shorter period. The time constant may be reduced by implementing a large number of thermocouples or thermopile rods, thus increasing the packing density. The sensitivity is inversely related to the calibration constant and depends solely on the choice of thermocouple material, the cross-sectional area, and length of the wires or rods of the series thermocouples comprising the thermopiles. Greater sensitivity is achieved with rods having a smaller cross sectional area and a greater length. As is apparent, the sensitivity and time constant best suited for a particular application may be implemented by proper selection of the length, area, number, and material of the thermopile rods.

It should be noted that when testing a substance having a high power output upon combustion resulting in a very large temperature increase, the direct proportionality of the thermopile voltage deteriorates. For these large temperature increases, the thermopile voltage is related to the temperature difference by quadratic. The appropriate corrections may be made in the computer.

Heat of combustion determinations may be made in the calorimeter of the present invention in the manner set forth below. The unitary lids of the inner and outer copper boxes must first be removed while the entire calorimeter unit is outside of the water bath. The bomb is removed from the inner copper box, and a known quantity of test substance is loaded into the sample cup attached to the lid of the bomb. With the bomb lid replaced, and pressurized, the bomb is inserted into the inner copper box and the lids to the inner and outer copper boxes are secured with the lock to be water tight. The entire calorimeter is then placed in the water bath and allowed to reach an equilibrium temperature with the water bath. At all times the water in the water bath is maintained at a constant temperature approximately $\pm 0.0005$ K. by means of the stirrer and the heating and cooling coils.

When the computer senses that the entire system is at equilibrium temperature, the ignition wires are triggered and combustion of the test substance begins. As the test substance burns it heats up the bomb which in turn heats up the inner copper box, the heat being conducted through the oil or water conduction layer. The outer copper box remains at the constant temperature of the water bath infinite heat sink. Consequently, the temperature change across the thermopiles due to the temperature gradient between the inner and outer copper boxes creates a voltage which is transmitted through the digital voltmeter to the computer and recorded as a function of time. Ideally, all of the heat is transmitted by conduction through the thermopiles, convection and radiation being being minimized.

As is apparent, the temperature gradient recorded is independent of the amount of water in the water bath, so long as there is sufficient control of the water in the water bath to maintain a constant temperature. The present invention measures the amount of heat generated and not the amount of heat dissipated to the surrounding water.

The data is continuously recorded until the temperature at the inner copper box is again equal to the constant temperature of the outer copper box and the water bath. At this point, all of the heat has been transmitted by conduction through the thermopiles. If rapid results are required, the data corresponding to the cooling of the calorimeter can be extrapolated, using an exponential curve. Because the entire calorimeter is again at the constant temperature at the end of the test, no cooling is required prior to retesting. As a result, the device operates with a fast turnaround time.

The heat of combustion is then determined by integrating the curve of voltage versus time and multiplying by a calibration constant. For relatively small temperature increases, this calibration constant remains linear. For large temperature rises, a quadratic function must be applied to the data. The curve may be integrated using the trapezoidal rule or using a Voltage Frequency Converter in a manner well known in the art. All calculations are done by the computer. Because of the sophistication, an operator need not know any calorimetry. Additional minor corrections may be required to the data to compensate for energy input by the stirrers and the ignition process. These corrections too can be performed within the computer.

As is apparent, the calorimeter constituting the present invention is simple in construction and in operation.

Obviously, numerous modifications and variations of the present invention are possible in light of the above teachings. It is therefore to be understood that within the scope of the appended claims, the invention may be practiced otherwise than as specifically described herein.

What is claimed is:

1. A conduction-type macrocalorimeter for measuring heat energy emitted by a test substance comprising:
   a sensor box having an inner compartment, an outer compartment, and heat flow detecting means within a gap defined by said inner and outer compartments;

said inner compartment being of high thermal conductivity and diffusivity, and having interior and exterior surfaces, said interior surface completely containerizing said test substance;

said outer compartment being of high thermal conductivity and diffusivity, and having interior and exterior surfaces, said exterior surface defining the outermost extent of said sensor box, said interior surface of said outer compartment closely conforming to said exterior surface of said inner compartment and completely containerizing said inner compartment;

said gap surrounding said inner compartment and being defined by said exterior surface of said inner compartment and said interior surface of said outer compartment, such that spacing between said gap defining surfaces remains substantially uniform;

heat flow detecting means for sensing heat flow from said test substance and generating a signal proportional to said heat flow, said heat flow detecting means being in intimate contact with said gap defining surfaces and substantially filling said gap to thereby minimize dead space within said gap;

a substantially infinite heat sink in intimate contact with said exterior surface of said outer compartment;

interpreting means for receiving said signal from said heat flow detecting means and generating an output related to said heat energy emitted from said test substance;

whereby substantially all said energy emitted by said test substance is transferred by conduction from said inner compartment to said outer compartment through said heat flow detecting means and dissipated to said substantially infinite heat sink.

2. A sensor box for a conduction-type macrocalorimeter comprising:

an inner compartment, an outer compartment, and heat flow detecting means within a gap defined by said inner and outer compartments;

said inner compartment being of high thermal conductivity and diffusivity, and having interior and exterior surfaces, said interior surface for completely containerizing a test substance;

said outer compartment being of high thermal conductivity and diffusivity, and having interior and exterior surfaces, said exterior surface defining the outermost extent of said sensor box, said interior surface of said outer compartment closely conforming to said exterior surface of said inner compartment and completely containerizing said inner compartment;

said gap surrounding said inner compartment and being defined by said exterior surface of said inner compartment and said interior surface of said outer compartment, such that spacing between said gap defining surfaces remains substantially uniform;

heat flow detecting means for sensing heat flow from said test substance and generating a signal proportional to said heat flow, said heat flow detecting means being in intimate contact with said gap defining surfaces and substantially filling said gap to thereby minimize dead space within said gap.

3. A conduction-type macrocalorimeter as set forth in claim 1, wherein said substantially infinite heat sink is a water bath, capable of being maintained at a substantially constant temperature.

4. A conduction-type macrocalorimeter as set forth in claim 1, wherein said heat flow detector means includes a plurality of series connected thermocouples.

5. A conduction-type macrocalorimeter as set forth in claim 1, wherein said test substance is further contained within a removable metallic bomb having means for igniting said test substance, said metallic bomb being surrounded by said inner compartment of said sensor box.

6. A conduction-type macrocalorimeter as set forth in claim 1, wherein said substantially infinite heat sink is a water bath, said test substance is further containerized within a removable metallic bomb, and said heat flow detecting means include a plurality of series connected thermocouples.

7. A conduction-type macrocalorimeter as set forth in claim 1, wherein said heat flow detecting means is a plurality of thermopiles.

8. A conduction-type macrocalorimeter as set forth in claim 1, wherein said inner and outer compartments each have a removable lid, said inner and outer compartment lids being removable as a unit.

9. A conduction-type macrocalorimeter as set forth in claim 1, further comprising means for rotating said sensor box about a vertical axis and means for tumbling said sensor box about a horizontal axis.

10. A conduction-type macrocalorimeter as set forth in claim 1, wherein said test substance is comprised of a first and a second substance, and further wherein said energy is emitted by a reaction caused by mixing of said first and second substances.

* * * * *